(12) United States Patent
Seong et al.

(10) Patent No.: US 12,266,110 B2
(45) Date of Patent: Apr. 1, 2025

(54) METHOD AND APPARATUS FOR PREDICTING REGION-SPECIFIC CEREBRAL CORTICAL CONTRACTION RATE ON BASIS OF CT IMAGE

(71) Applicants: KOREA UNIVERSITY RESEARCH AND BUSINESS FOUNDATION, Seoul (KR); SAMSUNG LIFE PUBLIC WELFARE FOUNDATION, Seoul (KR)

(72) Inventors: Jun Kyung Seong, Seoul (KR); Sang Won Seo, Seoul (KR); Jeong Hun Kim, Seoul (KR); Sihyeon Kim, Daejeon (KR)

(73) Assignees: KOREA UNIVERSITY RESEARCH AND BUSINESS FOUNDATION, Seoul (KR); SAMSUNG LIFE PUBLIC WELFARE FOUNDATION, Seoul (KR)

( * ) Notice: Subject to any disclaimer, the term of this patent is extended or adjusted under 35 U.S.C. 154(b) by 383 days.

(21) Appl. No.: 17/640,593

(22) PCT Filed: Sep. 2, 2020

(86) PCT No.: PCT/KR2020/011790
§ 371 (c)(1),
(2) Date: Mar. 4, 2022

(87) PCT Pub. No.: WO2021/045507
PCT Pub. Date: Mar. 11, 2021

(65) Prior Publication Data
US 2022/0335611 A1    Oct. 20, 2022

(30) Foreign Application Priority Data
Sep. 5, 2019   (KR) ........................ 10-2019-0109863

(51) Int. Cl.
*G06T 7/00*       (2017.01)
*A61B 6/50*       (2024.01)
(Continued)

(52) U.S. Cl.
CPC ............ *G06T 7/0014* (2013.01); *A61B 6/501* (2013.01); *G06T 7/11* (2017.01); *G06T 7/32* (2017.01);
(Continued)

(58) Field of Classification Search
CPC . G06T 7/0014; G06T 7/11; G06T 7/32; G06T 2207/10081; G06T 2207/10088;
(Continued)

(56) References Cited

U.S. PATENT DOCUMENTS

2011/0251479 A1*  10/2011  Relkin ................ A61B 5/0042
                                                                   600/411
2014/0328856 A1*  11/2014  Gelmont ............. C07K 16/065
                                                                   424/152.1

FOREIGN PATENT DOCUMENTS

KR    10-2018-0078033 A     7/2018
KR    10-1916347 B1        11/2018
(Continued)

OTHER PUBLICATIONS

International Search Report for PCT/KR2020/011790 dated Feb. 4, 2021 (PCT/ISA/210).
(Continued)

*Primary Examiner* — Umair Ahsan
(74) *Attorney, Agent, or Firm* — Sughrue Mion, PLLC

(57) ABSTRACT

The present invention relates to an apparatus for predicting a region-specific cerebral cortical contraction rate on the basis of a CT image. The present invention may comprise: a deep learning step of a deep learning network learning, by selecting and using CT images of a plurality of patients and
(Continued)

segmentation information thereof, a correlation between the CT images and the segmentation information; a feature extraction step of extracting, on the basis of each piece of the segmentation information, semantic feature information corresponding to the CT images; a machine learning step of a machine learning model learning, after a plurality of region-specific cerebral cortical contraction rates corresponding to each piece of the semantic feature information are additionally acquired, a correlation between the semantic feature information and the region-specific cerebral cortical contraction rates; a segmentation step of, when an image to be analyzed is input, acquiring segmentation information corresponding to the image to be analyzed, through the deep learning network; and a prediction step of predicting and reporting, after semantic feature information corresponding to the image to be analyzed is extracted on the basis of the segmentation information, a region-specific cerebral cortical contraction rate corresponding to the semantic feature information through the machine learning model.

11 Claims, 5 Drawing Sheets

(51) Int. Cl.
 G06T 7/11 (2017.01)
 G06T 7/32 (2017.01)
 G06V 10/40 (2022.01)
 G06V 20/70 (2022.01)
(52) U.S. Cl.
 CPC .............. *G06V 10/40* (2022.01); *G06V 20/70* (2022.01); *G06T 2207/10081* (2013.01); *G06T 2207/10088* (2013.01); *G06T 2207/20081* (2013.01); *G06T 2207/30016* (2013.01)
(58) Field of Classification Search
 CPC . G06T 2207/20081; G06T 2207/30016; G06T 2207/10104; G06T 2207/20076; G06T 2207/20084; G06T 7/0012; A61B 6/501; A61B 5/4088; A61B 5/7267; A61B 6/5247; A61B 6/5217; A61B 6/032; A61B 5/055; A61B 6/54; G06V 10/40; G06V 20/70; G06N 3/045; G06N 7/01; G06N 3/08; G06N 3/042; G16H 30/40; G16H 50/20; G16H 50/70
 See application file for complete search history.

(56) References Cited

FOREIGN PATENT DOCUMENTS

| KR | 10-1936302 B1 | | 1/2019 | |
| KR | 1936302 B1 | * | 1/2019 | ........... A61B 5/4803 |
| KR | 10-2019-0088730 A | | 7/2019 | |
| KR | 10-2001398 B1 | | 7/2019 | |
| WO | 2007/114238 A1 | | 10/2007 | |
| WO | 2012/032940 A1 | | 3/2012 | |
| WO | 2019/044089 A1 | | 3/2019 | |

OTHER PUBLICATIONS

Office Action issued Mar. 7, 2023 in Japanese Application No. 2022-514861.
Extended European Search Report issued Feb. 24, 2023 in European Application No. 20861207.7.
Ahmed MD Rishad et al: "Neuroimaging and Machine Learning for Dementia Diagnosis: Recent Advancements and Future Prospects", IEEE Reviews in Biomedical Engineering, vol. 12, Feb. 15, 2019 (Feb. 15, 2019), pp. 19-33, XP011710346, ISSN: 1937-3333, DOI: 10.1109/RBME.2018.2886237 [retrieved on Feb. 15, 2019].
Kelly A Condefer et al: "Clinical utility of computed tomography in the assessment of dementia: a memory clinic study", Apr. 13, 2004 (Apr. 13, 2004), International Journal of Geriatric Psychiatry, John Wiley and Sons, Chichester, GB, pp. 414-421, XP071722502, ISSN: 0885-6230.
Small et al: "Current and Future uses of neuroimaging for cognitively impaired patients", The Lancet Neurology, Elsevier, Amsterdam, NL, vol. 7, No. 2, Jan. 18, 2008 (Jan. 18, 2008), pp. 161-172, XP022427033, ISSN: 1474-4422, DOI: 10.1016/S1474-4422(08)70019-X.
Hattori Masumi et al: "Automated measurement of medial temporal lobe atrophy by computed tomography", International Journal of Computer Assisted Radiology and Surgery, Springer, DE, vol. 1, No. 6, Feb. 17, 2007 (Feb. 17, 2007), pp. 321-330, XP037873242, ISSN: 1861-6410, DOI: 10.1007/S11548-007-0071-Y [retrieved on Feb. 17, 2007].

* cited by examiner

[FIG. 1]
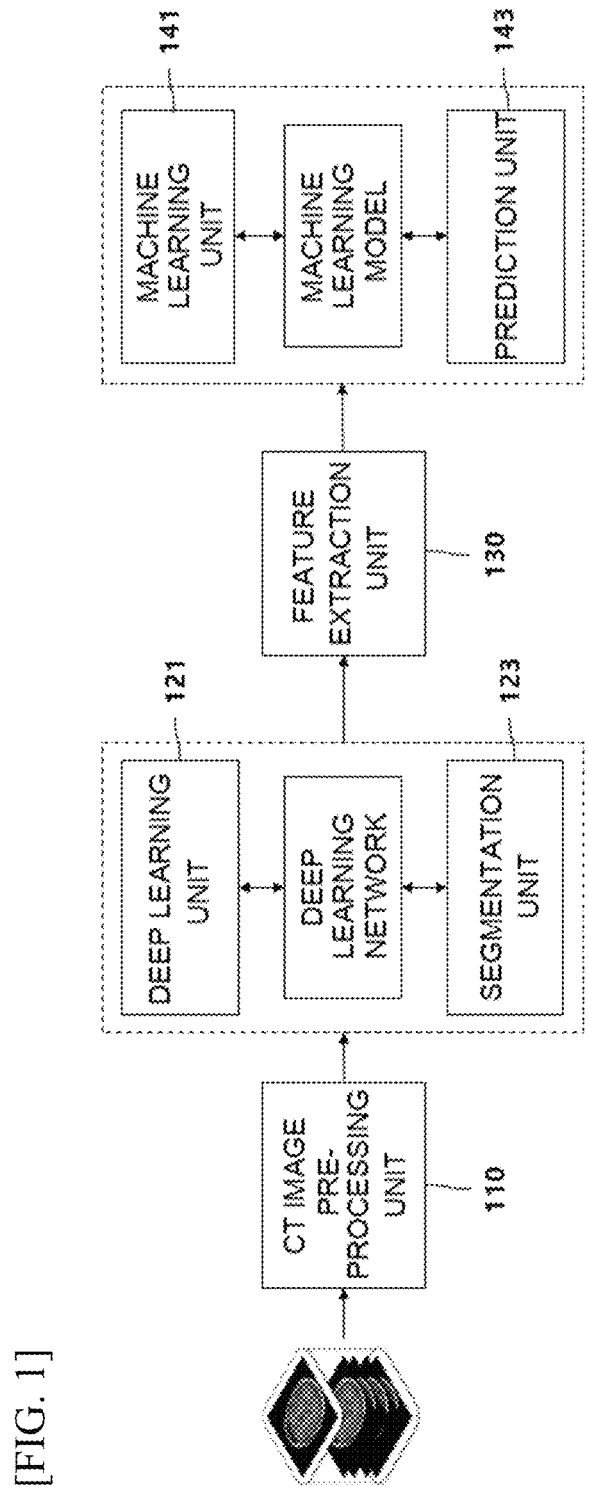

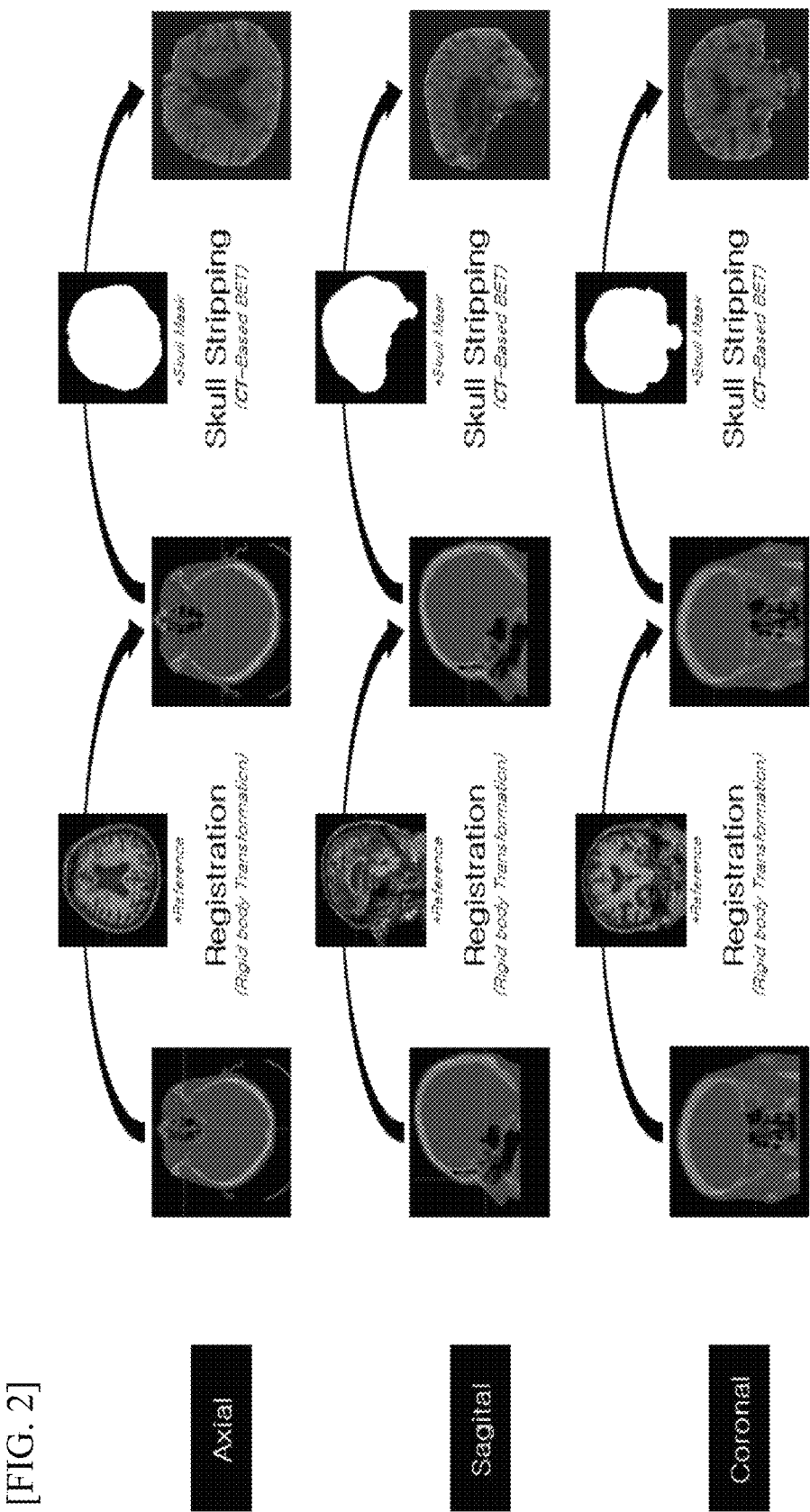
[FIG. 2]

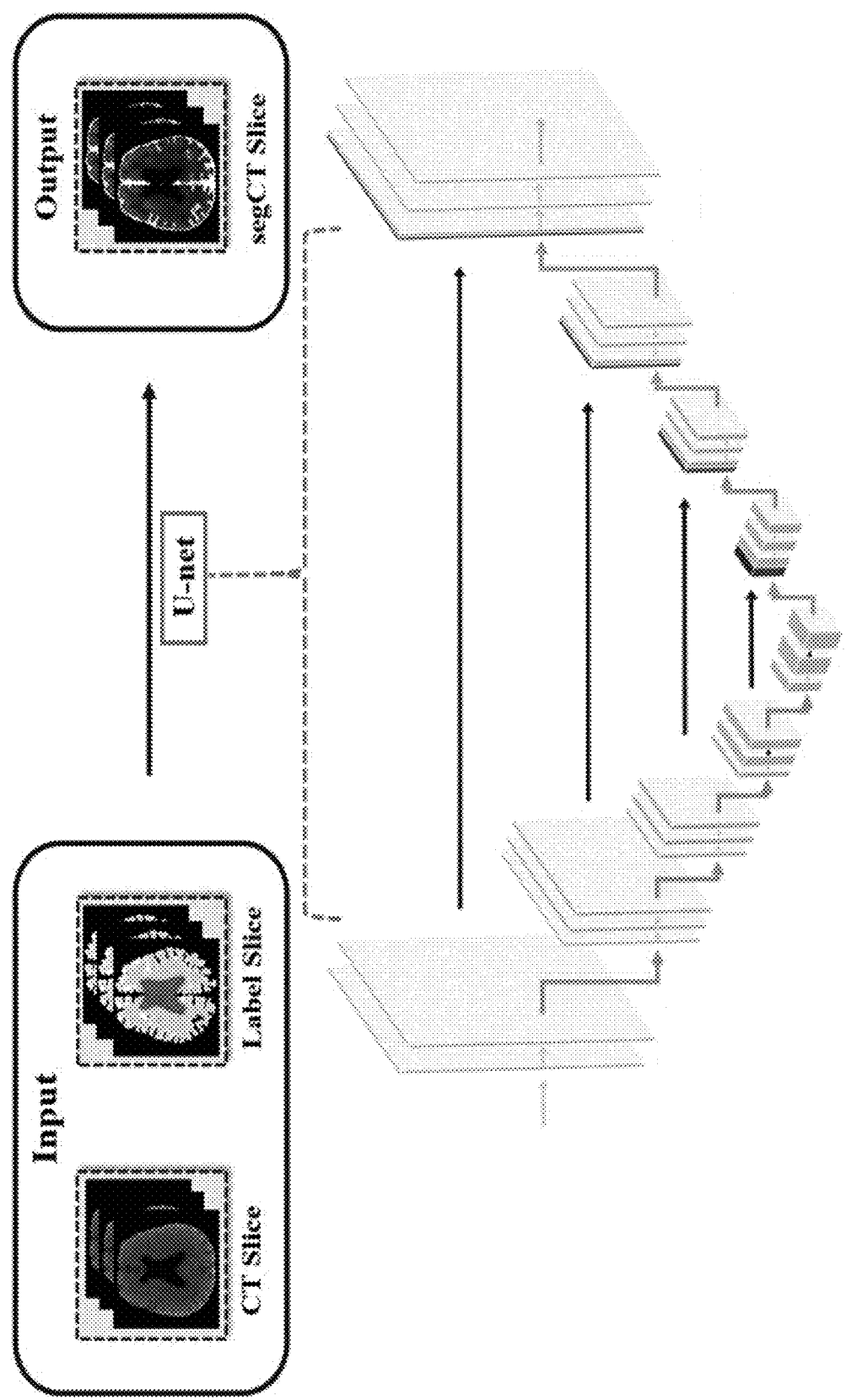
[FIG. 3]

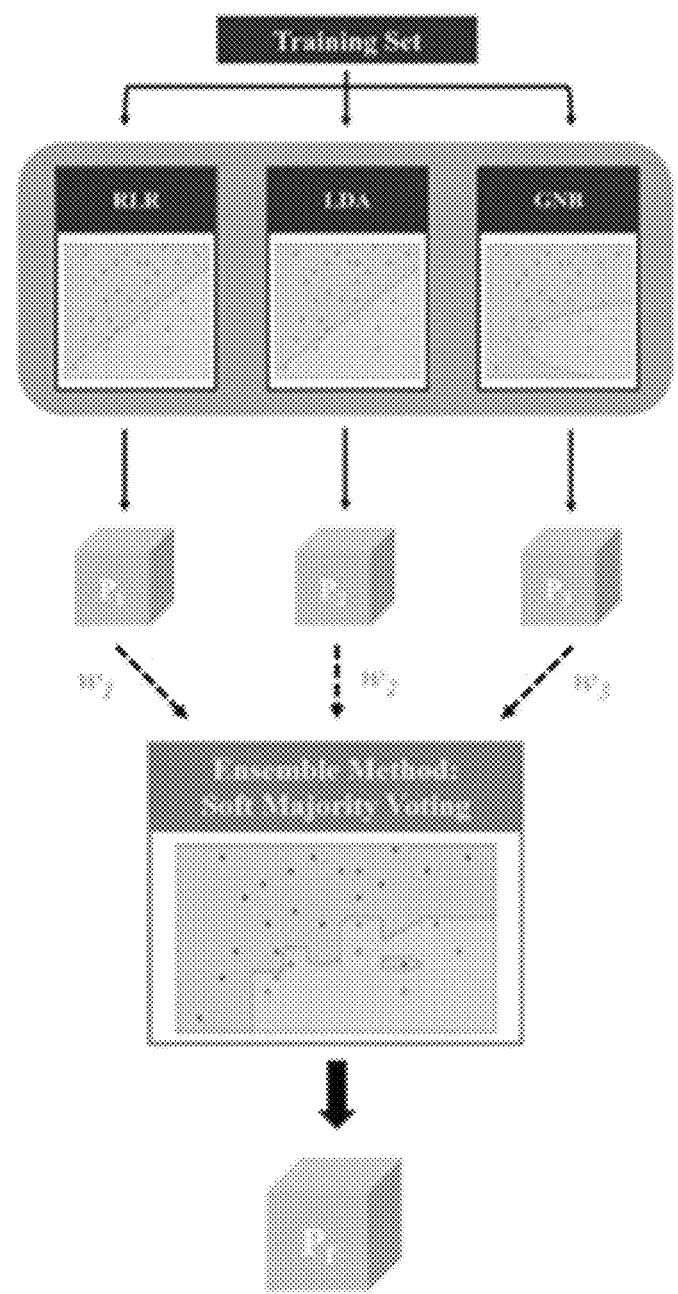
[FIG. 4]

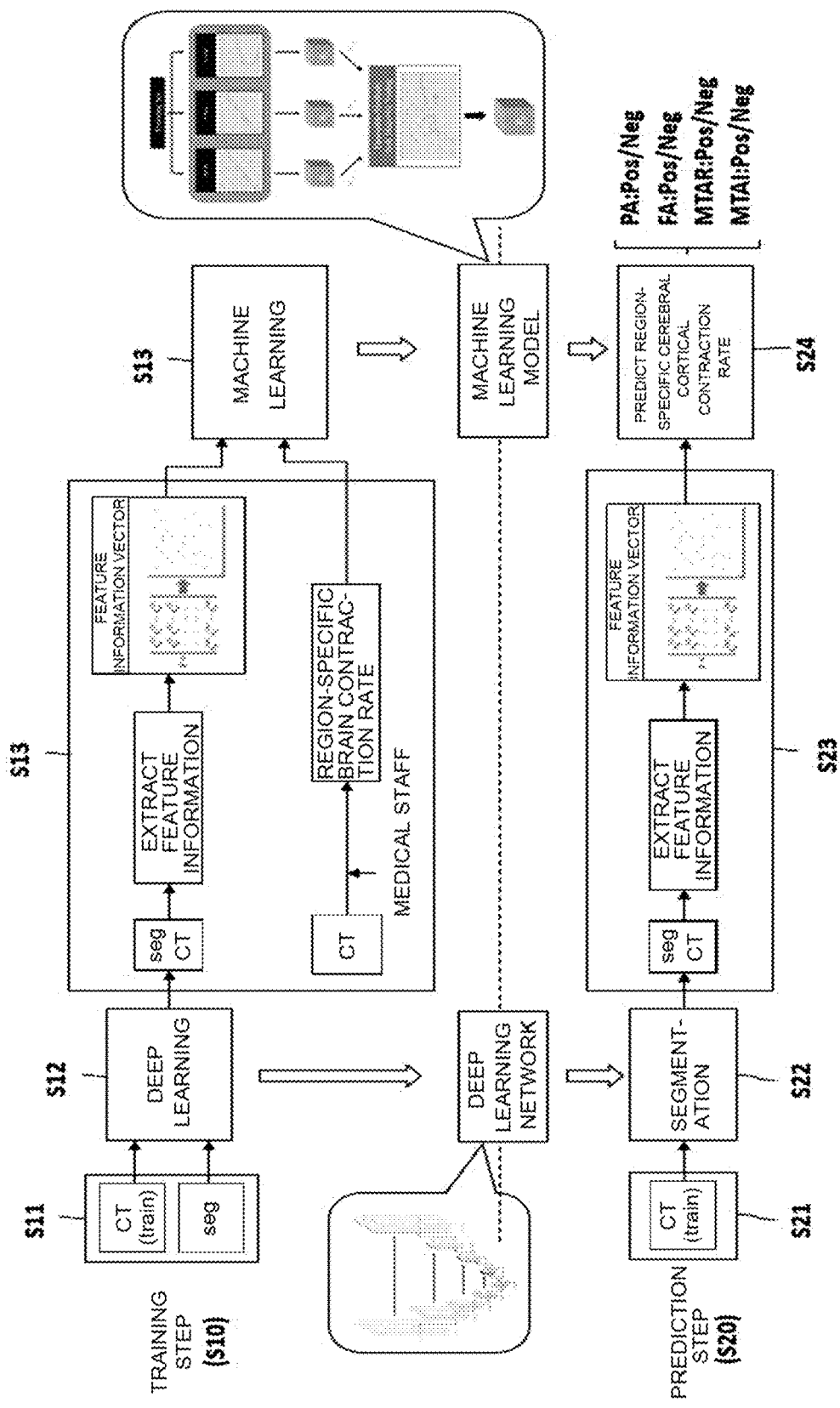
[FIG. 5]

METHOD AND APPARATUS FOR PREDICTING REGION-SPECIFIC CEREBRAL CORTICAL CONTRACTION RATE ON BASIS OF CT IMAGE

CROSS REFERENCE TO RELATED APPLICATIONS

This application is a National Stage of International Application No. PCT/KR2020/011790 filed Sep. 2, 2020, claiming priority based on Korean Patent Application No. 10-2019-0109863 filed Sep. 5, 2019.

TECHNICAL FIELD

The present disclosure relates to an apparatus for predicting a region-specific cerebral cortical contraction rate on the basis of a computed tomography (CT) image, which may predict a region-specific cerebral cortical contraction rate by using a CT image, instead of a magnetic resonance imaging (MRI) image, by using deep learning and machine learning technology.

BACKGROUND ART

Dementia is a chronic and progressive brain syndrome, and is a typical organic mental disorder of old age which is accompanied by disorders of cognitive functions including memory and executive ability, emotional disorders, and behavioral control disorders due to the occurrence and progression of brain lesions, and negatively impacts the ability to independently carry out everyday activities. Dementia may be caused by various brain injuries, but the most representative cause is Alzheimer's dementia, which accounts for 71% of all dementia types.

Although the exact cause of Alzheimer's disease is not yet known, it is known that due to increased production of beta-amyloid proteins and decreased emission, beta-amyloid proteins are deposited and amyloid plaques are formed, resulting in extensive neuronal destruction through interaction with other factors.

Accordingly, a method of diagnosing Alzheimer's disease by obtaining a positron emission tomography (PET) image through a PET-computed tomography (CT) device and analyzing and evaluating the accumulation of beta-amyloid based on the PET image has been proposed.

However, the method has a disadvantage in that the PET-CT device additionally provides a CT image in addition to the PET image, but the CT image is not used at all to diagnose Alzheimer's disease. In particular, when diagnosing Alzheimer's disease, it is necessary to additionally check a region-specific cerebral cortical contraction rate. Because this information may not be provided through the CT image, the information should be obtained and provided by obtaining and analyzing a magnetic resonance imaging (MRI) image through a separate MRI device.

DISCLOSURE

Technical Problem

To solve the above problems, the present disclosure provides an apparatus for predicting a region-specific cerebral cortical contraction rate on the basis of a computed tomography (CT) image, which may predict a region-specific cerebral cortical contraction rate by using a CT image, instead of a magnetic resonance imaging (MRI) image, by using deep learning and machine learning technology.

Objectives of the present disclosure are not limited thereto, and other unmentioned objectives will be clearly understood by one of ordinary skill in the art to which the present disclosure pertains from the following description.

Technical Solution

To solve the problems, according to an embodiment of the present disclosure, a method of predicting a region-specific cerebral cortical contraction rate on basis of a computed tomography (CT) image includes: a deep learning step of training a deep learning network, by selecting and using CT images of a plurality of patients and segmentation information, about a correlation between the CT images and the segmentation information; a feature extraction step of extracting, on basis of each segmentation information, semantic feature information corresponding to each of the CT images; a machine learning step of additionally obtaining a region-specific cerebral cortical contraction rate corresponding to each semantic feature information and then training a machine learning model about a correlation between the semantic feature information and the region-specific cerebral cortical contract rate; a segmentation step of, when an image to be analyzed is input, obtaining segmentation information corresponding to the image to be analyzed through the deep learning network; and a prediction step of extracting semantic feature information corresponding to the image to be analyzed on basis of the segmentation information and then predicting and notifying a region-specific cerebral cortical contraction rate corresponding to the semantic feature information through the machine learning model.

The deep learning network may be implemented as a U-net model.

The segmentation information may include white matter region information, gray matter region information, and ventricular region information.

The semantic feature information may include a three-dimensional (3D) volume ratio of white matter, a 3D volume ratio of gray matter, a sum of 3D volume ratios of white matter and gray matter, a 3D volume of ventricle, a two-dimensional (2D) area ratio of white matter, a 2D area ratio of gray matter, a sum of 2D area ratios of white matter and gray matter, and a 2D area of ventricle.

The machine learning model may be implemented as a soft majority voting model using at least one of a regularized logistic regression model, a linear discriminant analysis model, and a Gaussian Naïve Bayes model.

The method may further include, when CT images of a plurality of patients or an image to be analyzed are input, performing an image pre-processing operation by performing image registration through rigid body transformation and then removing a skull image.

To solve the problems, according to another embodiment of the present disclosure, an apparatus for predicting a region-specific cerebral cortical contraction rate on basis of a computed tomography (CT) image includes: a CT image pre-processing unit configured to, when CT images of a plurality of patients or an image to be analyzed are input, perform image registration through rigid body transformation and then remove a skull image; a deep learning unit configured to additionally obtain each segmentation information corresponding to each of the CT images and then train a deep learning network about a correlation between the CT image and the segmentation information; a segmentation unit configured to obtain and output segmentation information corresponding to the image to be analyzed through the deep learning network; a feature extraction unit configured to extract semantic feature information corresponding to each CT image or the image to be analyzed based on each segmentation information; a machine learning unit configured to additionally obtain a region-specific cerebral cortical contraction rate corresponding to each semantic feature information of the CT image and then train a machine learning model about a correlation between the semantic feature information and the region-specific cerebral cortical contraction rate; and a prediction unit configured to predict and notify a region-specific cerebral cortical contraction rate corresponding to the semantic feature information of the image to be analyzed through the machine learning model.

The deep learning network may be implemented as a U-net model.

The segmentation information may include white matter region information, gray matter region information, and ventricular region information.

The semantic feature information may include a three-dimensional (3D) volume ratio of white matter, a 3D volume ratio of gray matter, a sum of 3D volume ratios of white matter and gray matter, a 3D volume of ventricle, a two-dimensional (2D) area ratio of white matter, a 2D area ratio of gray matter, a sum of 2D area ratios of white matter and gray matter, and a 2D area of ventricle.

The machine learning model may be implemented as a soft majority voting model using at least one of a regularized logistic regression model, a linear discriminant analysis model, and a Gaussian Naïve Bayes model.

Advantageous Effects

According to the present disclosure, a segmented computed tomography (CT) image may be obtained through a deep learning network, and a region-specific cerebral cortical contraction rate may be more rapidly and accurately predicted through a machine learning module.

As a result, both a PET image and a CT image obtained through a positron emission tomography (PET)-CT device may be used to diagnose Alzheimer's disease, and particularly, even a region-specific cerebral cortical contraction rate may be obtained and provided without using a separate magnetic resonance imaging (MRI) device.

DESCRIPTION OF DRAWINGS

FIG. 1 is a view illustrating an apparatus for predicting a region-specific cerebral cortical contraction rate on the basis of a computed tomography (CT) image, according to an embodiment of the present disclosure.

FIG. 2 is a view for describing a CT image pre-processing method, according to an embodiment of the present disclosure.

FIG. 3 is a view illustrating a deep learning network, according to an embodiment of the present disclosure.

FIG. 4 is a view illustrating a machine learning module, according to an embodiment of the present disclosure.

FIG. 5 is a view for describing a method of predicting a region-specific cerebral cortical contraction rate on the basis of a CT image, according to an embodiment of the present disclosure.

BEST MODE

The following description illustrates only a principle of the present disclosure. Therefore, one of ordinary skill in the art may implement the principle of the present disclosure and invent various devices included in the spirit and scope of the present disclosure although not clearly described or shown in the present specification. In addition, it is to be understood that all conditional terms and embodiments mentioned in the present specification are basically intended only to allow one of ordinary skill in the art to understand a concept of the present disclosure, and the present disclosure is not limited to embodiments and states particularly mentioned as such.

Further, it is to be understood that all detailed descriptions mentioning a specific embodiment of the present disclosure as well as principles, aspects, and embodiments of the present disclosure are intended to include structural and functional equivalences thereof. Further, it is to be understood that these equivalences include an equivalence that will be developed in the future as well as an equivalence that is current well-known, that is, all devices invented so as to perform the same function regardless of a structure.

Therefore, it is to be understood that, for example, a block diagram of the present specification shows an illustrative conceptual aspect for embodying a principle of the present disclosure. Similarly, it is to be understood that all flow-charts, state transition diagrams, pseudo-code, and the like, show various processes that may be tangibly embodied in a computer-readable medium and that are executed by computers or processors regardless of whether or not the computers or the processors are clearly shown.

Functions of various devices including processors or functional blocks represented as concepts similar to the processors and shown in the accompanying drawings may be provided by hardware having capability to execute appropriate software as well as dedicated hardware. When the functions are provided by the processors, they may be provided by a single dedicated processor, a single shared processor, or a plurality of individual processors and some of them may be shared.

In addition, terms mentioned as a processor, a control, or a concept similar to the processor or the control should not be interpreted to exclusively cite hardware having capability to execute software, but should be interpreted to implicitly include digital signal processor (DSP) hardware and a read-only memory (ROM), a random-access memory (RAM), and a non-volatile memory for storing software without being limited thereto. The above-mentioned terms may also include well-known other hardware.

In the claims of the present specification, components represented as means for performing functions mentioned in the detailed description are intended to include all methods for performing functions including all types of software including, for example, a combination of circuit devices performing these functions, firmware/micro code, or the like, and are coupled to appropriate circuits for executing the software so as to execute these functions. It is to be understood that because functions provided by variously mentioned means are combined with each other and are combined with a scheme demanded by the claims in the present disclosures defined by the claims, any means capable of providing these functions are equivalent to means recognized from the present specification.

The above-mentioned objectives, features, and advantages will become more obvious from the following detailed description provided in relation to the accompanying drawings. Therefore, one of ordinary skill in the art to which the present disclosure pertains may easily practice a technical idea of the present disclosure. Further, in describing the present disclosure, in the case in which it is judged that a detailed description of a well-known technology associated with the present disclosure may unnecessarily make the gist of the present disclosure unclear, it will be omitted.

FIG. 1 is a view illustrating an apparatus for predicting a region-specific cerebral cortical contraction rate on the basis of a computed tomography (CT) image, according to an embodiment of the present disclosure.

Referring to FIG. 1, an apparatus for predicting a region-specific cerebral cortical contraction rate of the present disclosure includes a CT image pre-processing unit 110, a deep learning unit 121, a segmentation unit 123, a feature extraction unit 130, a machine learning unit 141 and a prediction unit 143.

The CT image pre-processing unit 110 receives and pre-processes each pre-obtained CT image or CT image of a subject to be analyzed, and converts the image into an image capable of deep learning.

That is, by considering that a CT image is a plurality of cross-sectional images scanned in axial, sagittal, and coronal directions of the brain and each of the cross-sectional images has a different coordinate system according to a scanning direction, the plurality of cross-sectional images are registered through rigid body transformation as shown in FIG. 2 and a correlation between the cross-sectional images is identified. Next, a skull image included in the CT image is removed to leave only a brain tissue image (skull stripping).

Also, when necessary, intensity normalization and histogram equalization may be additionally performed to improve image quality.

The deep learning unit 121 generates a plurality of training data including a pre-processed CT image and segmentation information corresponding to the pre-processed CT image, and trains a deep learning network through the training data.

In this case, the deep learning network may be implemented as a convolutional neural network (CNN) or a U-net, and particularly, it is more preferable that the deep learning network is implemented as a U-net having strengths in image segmentation and labeling. The U-net is an artificial neural network including multiple convolutional layers having a U shape as shown in FIG. 3, and has strengths in image segmentation and labeling.

The segmentation information includes white matter region information, gray matter region information, and ventricular region information, and may be obtained as a result of analyzing a magnetic resonance imaging (MRI) image corresponding to the CT image through an image segmentation program such as a Freesurfer or by training and verifying segmentation information manually input by a user through the deep learning network.

When an image to be analyzed (i.e., a CT image of a subject to be analyzed) is input, the segmentation unit 123 automatically obtains segmentation information corresponding to the image to be analyzed through the deep learning network whose training is completed, and generates and outputs a CT image including the segmentation information, that is, a segmented CT image.

The feature extraction unit 130 extracts semantic feature information from the segmented CT image.

The semantic feature information may include at least one of (1) a three-dimensional (3D) volume ratio of white matter, (2) a 3D volume ratio of gray matter, (3) a sum of 3D volume ratios of white matter and gray matter, (4) a 3D volume of ventricle, (5) a two-dimensional (2D) area ratio of white matter, (6) a 2D area ratio of gray matter, (7) a sum of 2D area ratios of white matter and gray matter, and (8) a 2D area of ventricle.

In more detail, the feature extraction unit 130 converts the CT image into a 3D volume image, divides a region of the 3D volume image into a white matter region, a gray matter region, and a ventricular region according to the segmentation information included in the CT image, and extracts 3D volume ratios of white matter, gray matter, and ventricle (1), (2), (4) through their volume values.

The feature extraction unit 130 selects a CT image just before the ventricle is observed while axially scanning the 3D volume image from top to bottom, and then extracts 2D area ratios of white matter and gray matter (5), (6) based on the CT image.

Finally, the feature extraction unit 130 selects a CT image in which the largest ventricle is observed while axially scanning the 3D volume image from top to bottom, and then extracts a 2D area of ventricle (8) based on the CT image.

The machine learning unit 141 generates a plurality of training data including semantic feature information and a region-specific cerebral cortical contraction rate corresponding to the semantic feature information, and trains a machine learning model through the training data. In this case, the region-specific cerebral cortical contraction rate may be a value directly measured by medical staff by referring to the CT image, and may be, for example, a cerebral cortical contraction rate in four regions of the brain related to Alzheimer's disease (frontal, parietal, and medial temporal lobes of the left and right).

The machine learning model of the present disclosure may be implemented as a soft majority voting (SMV) model using at least one of a regularized logistic regression (RLR) algorithm, a linear discriminant analysis (LDA) algorithm, and a Gaussian Naïve Bayes (GNB) algorithm, as shown in FIG. 4.

For reference, the RLR algorithm is an algorithm to which regularization is applied to prevent a model in a general regression algorithm from being underfitted or overfitted, and particularly, L2 regularization from among various regularization methods is used in the present disclosure.

The LDA algorithm is a probabilistic generative model among machine learning algorithms, and is an algorithm that classifies data into a group when the squared distance between observed data and central (mean) data is the minimum.

The GNB algorithm is an algorithm that uses a Gaussian function as a kernel function in a naïve Bayes algorithm that creates a classifier using Bayes' theorem that assumes independence between features among machine learning algorithms.

The SMV model is a model that corresponds to an aggregation method among ensemble models of machine learning, and is an algorithm that determines a final class by giving weights based on a sum of conditional probabilities of individual classifiers and then voting by majority vote. The SMV model has improved performance when compared to a simple direct majority voting model.

When the semantic feature information of the image to be analyzed is input, the prediction unit 143 automatically obtains and outputs a region-specific cerebral cortical contraction rate corresponding to the semantic feature information of the image to be analyzed through the machine learning model whose training is completed.

A method of predicting a region-specific cerebral cortical contraction rate on the basis of a CT image of the present disclosure will be described with reference to FIG. 5.

As shown in FIG. 5, a method of predicting a region-specific cerebral cortical contraction rate of the present disclosure roughly includes a training step S10 and a prediction step S20.

First, in a training data generation step S11, CT images (train) of a plurality of patients are obtained and pre-processed by accessing a medical information database in which medical information, medical treatment result information, and diagnostic information of a plurality of patients are stored.

Also, segmentation information seg corresponding to each of the CT images is additionally obtained. When segmentation information of an MRI image corresponding to a CT image is stored in the medical information database, the segmentation information is used as it is. When only an MRI image is stored, segmentation information including white matter region information, gray matter region information, and ventricular region information is extracted and used from the MRI image through a known image segmentation program. In contrast, when there is no MRI image and no segmentation information of the MRI image, the information is manually received from a user.

In a deep learning network training step S12, a plurality of training data having the CT image as an input condition and the segmentation information as an output condition are generated, and then a deep learning network is trained about a correlation between the CT image and the segmentation information through the training data. In the case of a U-net, deep learning is performed by using a stochastic gradient descent algorithm, and a stopping point is selected by applying a training early stopping method.

In a machine learning model training step S13, semantic feature information corresponding to each CT image is extracted based on each segmentation information, and a region-specific cerebral cortical contraction rate corresponding to each CT image is obtained. In this case, the cerebral cortical contract rate may be a value measured by medical staff by referring to the CT image.

A plurality of training data having the semantic feature information as an input condition and the region-specific cerebral cortical contraction rate as an output condition are generated, and then a machine learning model is trained through the training data.

When the training step S10 is completed, the prediction step S20 may be performed.

In an analysis target image input step S21 of the prediction step S20, an image to be analyzed (i.e., a CT image of a subject to be analyzed) provided from a PET-CT device is received and stored.

In a segmentation step S22, segmentation information corresponding to the image to be analyzed is obtained through the deep learning network.

In a feature information extraction step S23, semantic feature information corresponding to the image to be analyzed is extracted based on the segmentation information obtained in operation S22.

Finally, in a prediction step S24, a region-specific cerebral cortical contraction rate corresponding to the semantic feature information is obtained and output through the machine learning model.

The method according to the present embodiment may be embodied as a program executed in a computer and may be stored in a computer-readable recording medium, and examples of the computer-readable recording medium include read-only memories (ROMs), random-access memories (RAMs), compact disc (CD)-ROMs, magnetic tapes, floppy disks, optical data storage devices, and carrier waves (e.g., data transmission through the Internet).

The computer-readable recording medium may be distributed among computer systems that are interconnected through a network so that computer-readable code is stored and executed in a distributed fashion. Functional programs, code, and code segments for embodying the method may be easily derived by programmers in the technical field to which the present disclosure pertains.

In addition, although preferred embodiments of the present disclosure have been illustrated and described above, the present disclosure is not limited to the above-described specific embodiments. Various modified embodiments may be made by one of ordinary skill in the art without departing from the scope of the present disclosure as claimed in the claims, and these modifications should not be individually understood from the technical spirit or the prospect of the present disclosure.

The invention claimed is:

1. A method of predicting a region-specific cerebral cortical contraction rate on basis of a computed tomography (CT) image, the method comprising: a deep learning step of training a deep learning network, by selecting and using CT images of a plurality of patients and segmentation information, about a correlation between the CT images and the segmentation information; a feature extraction step of extracting, on basis of each segmentation information, semantic feature information corresponding to each of the CT images; a machine learning step of additionally obtaining a region-specific cerebral cortical contraction rate corresponding to each semantic feature information and then training a machine learning model about a correlation between the semantic feature information and the region-specific cerebral cortical contract rate; a segmentation step of, when an image to be analyzed is input, obtaining segmentation information corresponding to the image to be analyzed through the deep learning network; and a prediction step of extracting semantic feature information corresponding to the image to be analyzed on basis of the segmentation information and then predicting and notifying a region-specific cerebral cortical contraction rate corresponding to the semantic feature information through the machine learning model.

2. The method of predicting a region-specific cerebral cortical contraction rate on basis of a CT image of claim 1, wherein the deep learning network is implemented as a U-net model.

3. The method of predicting a region-specific cerebral cortical contraction rate on basis of a CT image of claim 1, wherein the segmentation information is extracted based on a magnetic resonance imaging (MRI) image, and comprises white matter region information, gray matter region information, and ventricular region information.

4. The method of predicting a region-specific cerebral cortical contraction rate on basis of a CT image of claim 1, wherein the semantic feature information comprises a three-dimensional (3D) volume ratio of white matter, a 3D volume ratio of gray matter, a sum of 3D volume ratios of white matter and gray matter, a 3D volume of ventricle, a two-dimensional (2D) area ratio of white matter, a 2D area ratio of gray matter, a sum of 2D area ratios of white matter and gray matter, and a 2D area of ventricle.

5. The method of predicting a region-specific cerebral cortical contraction rate on basis of a CT image of claim 1, wherein the machine learning model is implemented as a soft majority voting model using at least one of a regularized logistic regression model, a linear discriminant analysis model, and a Gaussian Naïve Bayes model.

6. The method of predicting a region-specific cerebral cortical contraction rate on basis of a CT image of claim 1, further comprising, when CT images of a plurality of patients or an image to be analyzed are input, performing an image pre-processing operation by performing image registration through rigid body transformation and then removing a skull image.

7. An apparatus for predicting a region-specific cerebral cortical contraction rate on basis of a computed tomography (CT) image, the apparatus comprising: a CT image pre-processing unit configured to, when CT images of a plurality of patients or an image to be analyzed are input, perform image registration through rigid body transformation and then remove a skull image; a deep learning unit configured to additionally obtain each segmentation information corresponding to each of the CT images and then train a deep learning network about a correlation between the CT image and the segmentation information; a segmentation unit configured to obtain and output segmentation information corresponding to the image to be analyzed through the deep learning network; a feature extraction unit configured to extract semantic feature information corresponding to each CT image or the image to be analyzed based on each segmentation information; a machine learning unit configured to additionally obtain a region-specific cerebral cortical contraction rate corresponding to each semantic feature information of the CT image and then train a machine learning model about a correlation between the semantic feature information and the region-specific cerebral cortical contraction rate; and a prediction unit configured to predict and notify a region-specific cerebral cortical contraction rate corresponding to the semantic feature information of the image to be analyzed through the machine learning model.

8. The apparatus for predicting a region-specific cerebral cortical contraction rate on basis of a CT image of claim 7, wherein the deep learning network is implemented as a U-net model.

9. The apparatus for predicting a region-specific cerebral cortical contraction rate on basis of a CT image of claim 7, wherein the segmentation information comprises white matter region information, gray matter region information, and ventricular region information.

10. The apparatus for predicting a region-specific cerebral cortical contraction rate on basis of a CT image of claim 7, wherein the semantic feature information comprises a three-dimensional (3D) volume ratio of white matter, a 3D volume ratio of gray matter, a sum of 3D volume ratios of white matter and gray matter, a 3D volume of ventricle, a two-dimensional (2D) area ratio of white matter, a 2D area ratio of gray matter, a sum of 2D area ratios of white matter and gray matter, and a 2D area of ventricle.

11. The apparatus for predicting a region-specific cerebral cortical contraction rate on basis of a CT image of claim 7, wherein the machine learning model is implemented as a soft majority voting model using at least one of a regularized logistic regression model, a linear discriminant analysis model, and a Gaussian Naïve Bayes model.

\* \* \* \* \*